United States Patent [19]

Lee

[11] 4,154,230

[45] May 15, 1979

[54] EKG AND ULTRASONOSCOPE DISPLAY

[75] Inventor: Robert D. Lee, San Mateo, Calif.

[73] Assignee: The United States of America as represented by the Administrator of the National Aeronautics and Space Administration, Washington, D.C.

[21] Appl. No.: 759,965

[22] Filed: Jan. 17, 1977

[51] Int. Cl.$^2$ .............................................. A61B 5/02
[52] U.S. Cl. .................................... 128/661; 128/700; 128/712
[58] Field of Search ............ 128/2 V, 2.05 Z, 2.06 G; 73/606, 610; 340/324 AD

[56] References Cited

U.S. PATENT DOCUMENTS

| | | | |
|---|---|---|---|
| 3,624,744 | 11/1971 | Manger | 128/2 V X |
| 3,744,479 | 7/1973 | Stein et al. | 128/2 V X |
| 3,816,791 | 6/1974 | Fluegel | 340/324 AD X |
| 3,902,476 | 9/1975 | Hileman | 128/2 V |
| 3,936,791 | 2/1976 | Kossoff | 128/2 V X |
| 3,954,098 | 5/1976 | Dick et al. | 128/2 V X |
| 4,045,815 | 2/1976 | Griffith et al. | 340/324 AD X |

FOREIGN PATENT DOCUMENTS

2544094  5/1976  Fed. Rep. of Germany ...... 128/2.05 Z

OTHER PUBLICATIONS

Kikuchie, Y. et al., "Ultra-Sono-Cardio-Tomography," Japan Electronic Engr., Oct. 1970, No. 47, pp. 53–60.
Hertz, C. H., "Ultrasonic Engineering in Heart Diagnosis," Amer. Jrnl. of Cardiology, vol. 19, Jan. 1967, pp. 6–17.

*Primary Examiner*—Robert W. Michell
*Assistant Examiner*—Francis J. Jaworski
*Attorney, Agent, or Firm*—Darrell G. Brekke; John R. Manning; Armand McMillan

[57] ABSTRACT

A system is disclosed which permits simultaneous display of an EKG waveform in real time in conjunction with a two-dimensional cross-sectional image of the heart, so that the EKG waveform can be directly compared with dimensional changes in the heart. The apparatus of the invention includes an ultrasonoscope for producing a C-scan cross-sectional image of the heart. An EKG monitor circuit along with EKG logic circuitry is combined with the ultrasonoscope circuitry to produce on the same oscilloscope screen a continuous vertical trace showing the EKG waveform simultaneously with the heart image. The logic circuitry controls the oscilloscope display such that the display of both heart and EKG waveforms occurs on a real time basis.

7 Claims, 12 Drawing Figures

SAWTOOTH WAVEFORM

FIG.6B

GATED STAIRCASE WAVEFORM

FIG.6C

GATED SAWTOOTH WAVEFORM

EKG AND ULTRASONOSCOPE DISPLAY

ORIGIN OF THE INVENTION

The invention described herein was made by an employee of the United States Government and may be manufactured and used by or for the Government for Governmental purposes without the payment of any royalties thereon or therefor.

BACKGROUND OF THE INVENTION

1. Field of the Invention

The present invention relates generally to medical heart monitoring devices, and more particularly to an apparatus which permits simultaneous realtime display of a two-dimensional cross-sectional image of the heart with an EKG waveform.

2. Description of the Prior Art

In medical analysis of the heart, the use of EKG systems for analysis of the performance of the heart has long been a great aid in diagnosing potential heart disease. An additional apparatus which has recently been developed to further aid studies of the heart is the ultrasonoscope system disclosed in U.S. Pat. application Ser. No. 728,369, Biomedical Ultrasonoscope, Robert D. Lee, filed Sept. 30, 1976. This system is unique in that it is capable of providing a "C" mode heart scan as well as the conventional "A" and "M" scan modes. The "C" scan mode provides a cross-sectional image of the heart so that the actual movements in the heart can be visually observed.

Although the "C" mode heart scan in itself provides an important diagnostic tool, a real time display of both the "C" scan heart image and the corresponding EKG waveform on the same screen would provide a significant advantage over independent usage of the "C"-scan and conventional EKG monitoring. Specifically, simultaneous real time display of these two functions would allow a continuous check of the synchronization between dimensional changes of the heart and the periodicity of the EKG waveform. It is this goal of simultaneous display of both the heart image and the EKG waveform to which the present invention is directed.

SUMMARY OF THE INVENTION

Accordingly, one object of the present invention is to provide a novel apparatus for simultaneously displaying an image of the heart and an EKG waveform.

Another object of the present invention is the provision of a novel biomedical diagnostic instrument for checking synchronization between heart dimensional changes and EKG waveform periodicity.

A still further object of the present invention is the combination of an ultrasonoscope providing a "C" mode heart scan with circuitry for simultaneously displaying an EKG waveform.

Another object of the present invention is the provision of novel logic circuitry for allowing a simultaneous display of an EKG waveform and an image of the heart on the cathode ray tube.

Briefly, these and other objects of the present invention are achieved by the combination of an EKG monitoring circuit and appropriate logic with an ultrasonoscope of the type described in the above-referenced patent application. The logic circuitry includes an analog gating network for controlling an oscilloscope sweep so as to permit two separate displays during two separate time intervals. The displays are made to appear simultaneous by the use of high persistance phosphor on the face of an oscilloscope tube.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENT

Figure 1:
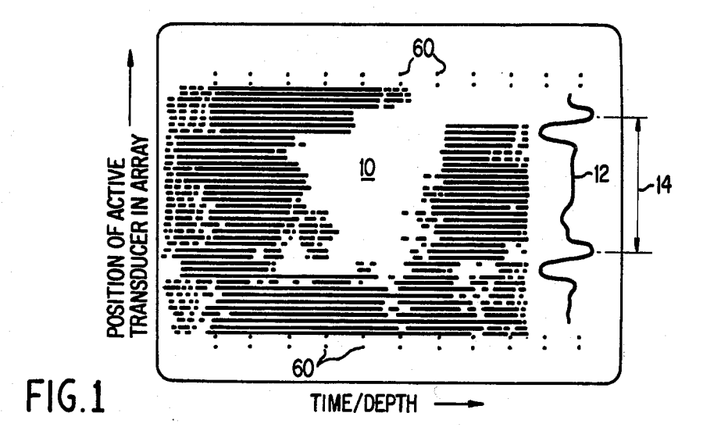
FIG. 1 is a representation of the display obtained when an ultrasonoscope is utilized in the "C" scan mode.

Referring now to the drawings, wherein like reference numerals designate identical or corresponding parts throughout the several views, and more particularly to FIG. 1 thereof, a typical "C" mode scan image is shown. In the "C" mode scan, the ultrasonoscope of the above-referenced patent application utilizes a linear array of ultrasonic transducers to project acoustic impulses toward the heart of a patient. Echo pulses are then detected to form a cross-sectional image of the heart. The vertical axis of the display illustrated in FIG. 1 represents the position of the active transducer in the transducer array, while the horizontal axis of the display represents time delay or depth. The signals sensed by the transducer after passing through the heart are applied to the Z axis input of a cathode ray tube, or conventional oscilloscope, for the purpose of modulating the intensity of the cathode ray tube trace. The result is the formation of an image, generally represented by the region 10, which effectively illustrates a cross section of the heart. The present invention adds to this "C" scan image an EKG trace 12 so that the synchronization between the period 14 of the EKG trace can be compared with dimensional changes in the heart image 10. Those familiar with the medical sciences, particularly with the science of heart disease analysis, will immediately recognize the highly significant contribution to medical diagnosis made possible by an apparatus which can produce the simultaneous images illustrated in FIG. 1.

Figure 2:
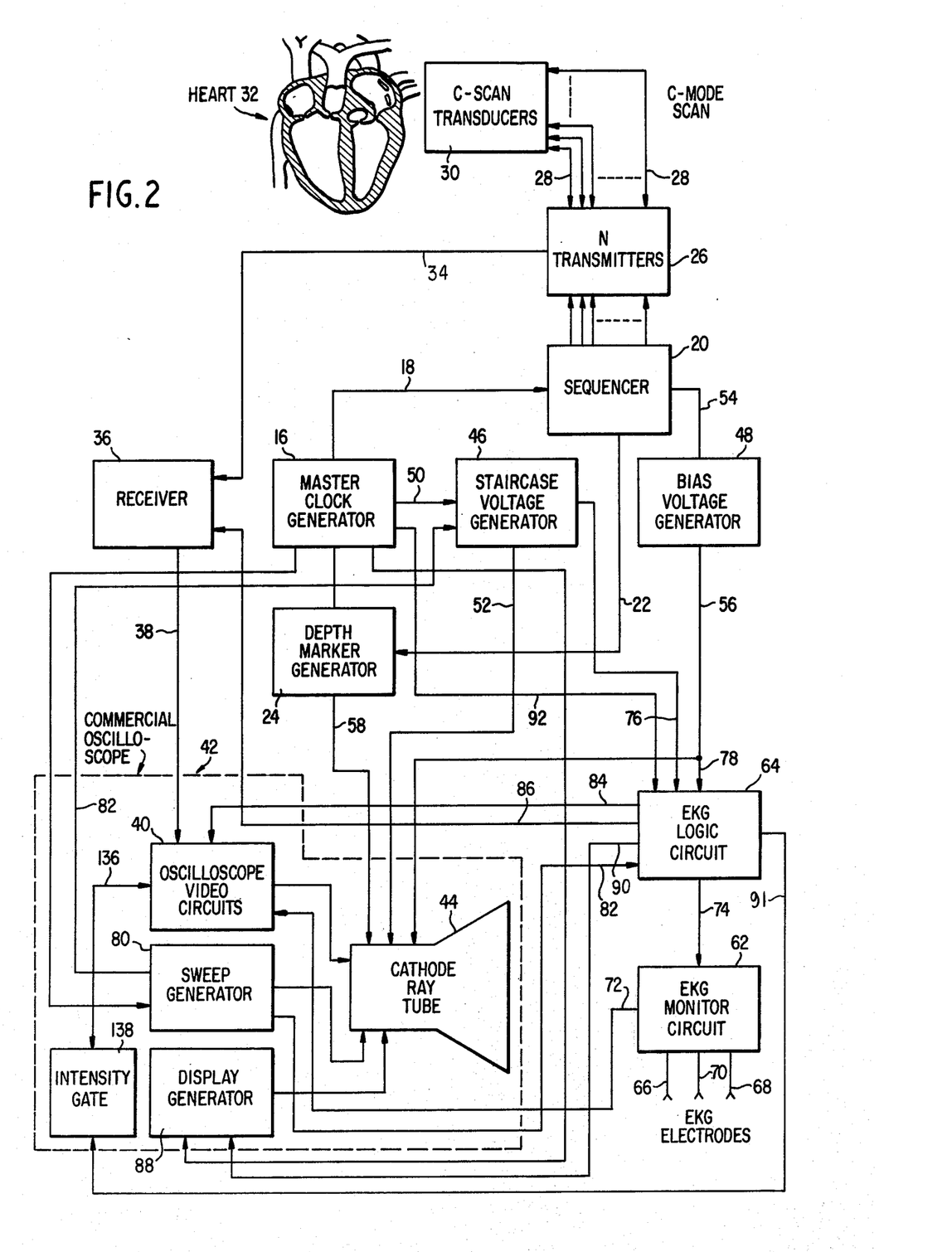
FIG. 2 is a comprehensive block diagram of the apparatus of the present invention.

The general arrangement of a system of the present invention is illustrated in the block diagram of FIG. 2.

The block diagram illustrates a "C" scan ultrasonoscope of the type disclosed in the above-referenced patent application, but modified to include the EKG display system of the present invention. Specifically, the system illustrated in FIG. 2 includes a master clock generator 16 which is coupled via a line 18 to a sequencer 20, the details of which are set forth in the above-identified patent application. The sequencer 20 is provided with a plurality of output terminals, N+4 in number, where N is a positive integer. The exact number of output terminals is determined by the desired resolution of the output display. In practice it has been found that 24 terminals is sufficient. The sequencer 20 is set by pulses from master clock generator 16 to initiate a trigger pulse at each one of the outputs of the sequencer in a predetermined time sequence. Two outputs of the sequencer, specifically the second and second from last, are connected via a line 22 to a depth marker generator 24. The two sequencer outputs connected to the depth marker generator result in the display of depth reference marks at the top and bottom of the displayed image of the heart for reference purposes.

The remaining outputs of the sequencer 20 are coupled to a plurality of N transmitters 26. These outputs are respectively taken from the third through the third-from-last output terminals of the sequencer 20. The result is that each N trigger pulses, after the first two in a sequence, fire the N transmitters 26 in cyclic order. Each transmitter transmits an electrical pulse over one of a plurality of lines 28 to a corresponding plurality of N transducers 30 arranged in a row and positioned on the skin of a patient's body. The transducers are actuated in a serial fashion by the pulses transmitted from the transmitters 26, each transducer converting the electrical input signal into an ultrasonic pulse which is radiated into the patient's body toward an internal organ such as the heart illustrated at 32. Echoes from the internal organ 32 are also sensed by the transducers 30 and are again converted into electrical signals which are fed back over the lines 28 through the transmitters 26 over a line 34 to a receiver 36. The receiver transmits the echo pulses over a line 38 to the video circuits 40 of an oscilloscope 42. The oscilloscope 42 is preferably a commercially available unit requiring a low input voltage level, such as an HP-1700 series unit manufactured by the Hewlett Packard Company of Palo Alto, California. The input signals applied to the oscilloscope 42 by the receiver 36 are displayed on the screen of a cathode ray tube 44 which is preferably equipped with a long persistence phosphorus.

The oscilloscope display is controlled by a staircase voltage generator 46 and a bias voltage generator 48. The staircase voltage generator 46, coupled to the master clock generator 16 via a line 50, is controlled by the master clock so that the incremental steps in the staircase voltage output of the staircase voltage generator 46 are in synchronism with the pulses from the master clock generator. The output of the staircase voltage generator is applied over a line 52 to the Y-axis input of the cathode ray tube 44 so as to separate the individual traces produced by the echo pulses applied to the Z-axis (intensity) inputs of the cathode ray tube from the receiver 36. The stepwise voltage is used to spread out the series of traces on the face of the oscilloscope tube in accordance with the positions of the transducers, as shown in FIG. 1.

The bias voltage generator 48 is used to further enhance the image displayed on the cathode ray tube screen. Specifically, the last output terminal of the sequencer 20 is connected via a line 54 to the bias voltage generator 48 so that the last trigger pulse in an individual sequence causes the bias voltage generator to produce a bias voltage which is applied over a line 56 to the Y-axis input of the cathode ray tube 44. This additional bias voltage is added to the staircase input voltage for offsetting the vertical position of the staircase voltage by half a raster line. This produces an additional set of scan lines between the scan lines produced by the staircase voltage generator for effectively enhancing the resolution of the CRT image. In other words, if 24 transducers are used, the bias voltage generator produces 48 scan lines on the face of the oscilloscope tube to enhance the resolution of the displayed heart image. In the C-scan system described in the above-mentioned application, the staircase voltage and the bias voltage are added at the Y-axis input of the CRT. In the C-scan system described ... CRT. Herein, ... CRT 44.

The previously mentioned depth marker generator 24 is also coupled via a line 58 to the Y-axis input of the cathode ray tube 44 for producing depth scale marks, as illustrated at 60 in FIG. 1. These marks may, for example, represent one centimeter increments in depth so that the oscilloscope image can be properly scaled and accurately related to dimensional changes in a patient's heart.

The system described thus far is the C-scan system described in the above-referenced patent application. Attention will now be directed to the modification of this circuitry which enables simultaneous display of the C-scan image and an EKG trace. It is noted that the additional circuitry may be coupled through an appropriate switching system to the circuitry described above so that it can be conveniently switched in and out of the system depending upon the desired use of the system. The required switching network can be easily understood by those skilled in the art, and accordingly has been omitted from the drawings for the purpose of clarity in the somewhat complicated innerconnection scheme shown.

The additional circuitry utilized in displaying the EKG trace includes an EKG monitor circuit 62 and an EKG logic circuit 64. The EKG monitor circuit includes two input electrodes 66 and 68 along with a reference electrode 70 which are coupled to a patient for taking direct EKG readings. The EKG monitor circuit is coupled via a line 72 to the oscilloscope video circuits 40 for displaying the EKG trace 12.

The EKG logic circuit 64 provides gating and control functions to both the EKG monitor circuit and the oscilloscope internal circuitry to provide separate display intervals for the C-scan image and the EKF trace. The EKG logic circuit is coupled to the EKG monitor circuit over a line 74 for controlling the application of the EKG monitor voltage to the oscilloscope. The EKG logic circuit similarly receives the input of the staircase voltage generator 46 via a line 76, an input from the bias voltage generator 48 via a line 78 and an input from a sweep generator 80 of the oscilloscope 42 via a line 82. In addition to the output line 74, the EKG logic circuit is also coupled to the oscilloscope video circuits 40 via a line 84, to the receiver 36 via a line 86, to a display generator 88 of the oscilloscope 42 via a line 90 and to an intensity gate 138 of the oscilloscope via a line 91. The EKG logic circuit serves to gate the signals applied to it for controlling the display sequence of the cathode ray tube to alternate between the C-scan image and the EKG trace, as will be described in more detail subsequently. It is noted that the EKG logic circuit also receives a timing reference from the master clock generator 16 via a line 92.

Figure 3:
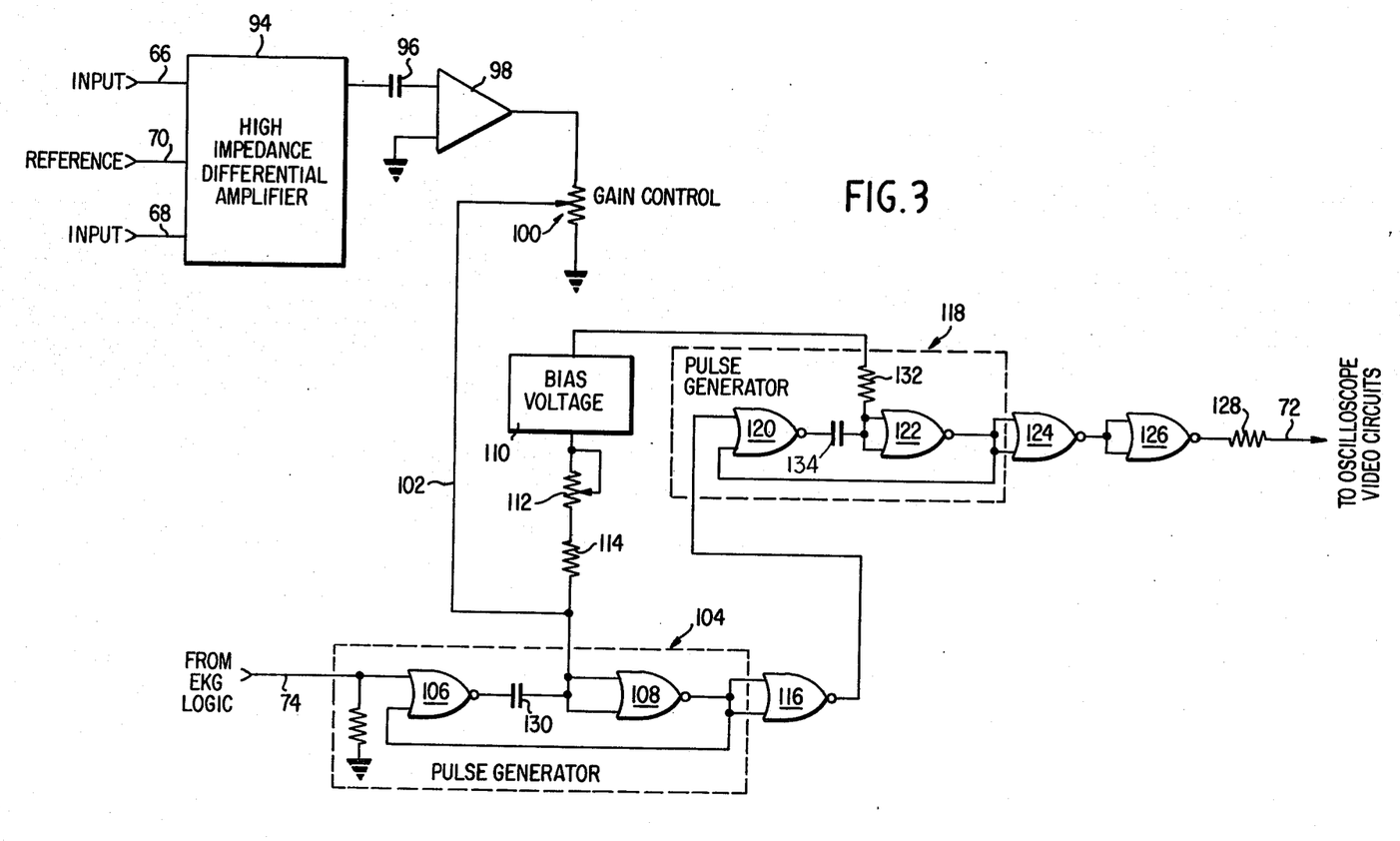
FIG. 3 is a schematic diagram of the EKG monitor circuit used in the system shown in FIG. 2.

Attention is now directed to FIG. 3 wherein the details of the EKG monitor circuit are illustrated. The EKG monitor circuit includes a high impedance differential amplifier 94 coupled to the input electrodes 66, 68 and the reference electrodes 70 which, as mentioned above, are coupled to the patient for detection electrical impulses produced by the heart. The output of the amplifier 94 is coupled through a capacitor 96 to an operational amplifier 98, the output of which is applied to a gain control potentiometer 100. The output from the gain control potentiometer is applied via a line 102 to one input of a pulse generator 104 formed of two interconnected NAND gates 106 and 108. Also coupled to the line 102, which is connected to the input of NAND gate 108, is a bias voltage source 110, preferably 10 volts. The bias voltage source is coupled through a position adjustment potentiometer 112 and a coupling resistor 114 to the input of NAND gate 108. The triggering input of the pulse generator 104 is received over a line 74 from the EKG logic circuit. This line is coupled to one input of the NAND gate 106.

The output of the pulse generator 104 is buffer amplifier through a suitably coupled NAND gate 116 and applied to a second pulse generator 118, also formed of a pair of interconnected NAND gates 120 and 122. This pulse generator is also coupled to the bias voltage source 110. The output of the pulse voltage generator 118 is double buffered by a pair of series connected NAND gates 124 and 126 interconnected to operate as buffer amplifiers. The output of the buffer amplifiers is connected through a coupling resistor 128 to the line 72 which applies the output of the EKG monitor circuit to the oscilloscope video circuit 40.

The operation of the EKG monitor circuit of FIG. 3 is such that the control pulse received from the EKG logic circuit over line 74 triggers the pulse generator 104 to produce a pulse, the duration of which represents the EKG position. The duration of this pulse is determined by the position control potentiometer 112 is conjunction with the coupling resistor 114 and by a capacitor 130 which couples the NAND gates 106 and 108. The width of the pulse is modulated by the EKG voltage waveform transmitted through the gain control potentiometer 110. The output of the pulse generator 104, which acts as a position generator, is buffer amplified and applied to the second pulse generator 118 which acts as a dot size generator. The dot size generator 118 regulates the pulse width which determines the EKG dot size on the CRT display in accordance with the value of a resistor 132 coupled to the input of NAND gate 112 and with the value of capacitor 134 coupling NAND gates 120 and 122. The output of this circuit is subsequently applied via line 72 to the oscilloscope video circuits which are in turn coupled via a line 136 to an intensity gate 138 of the oscilloscope 42. The intensity gate 138 controls the blanking of the EKG trace in conjunction with the blanking or display of the C-scan heart image.

Figure 4A:
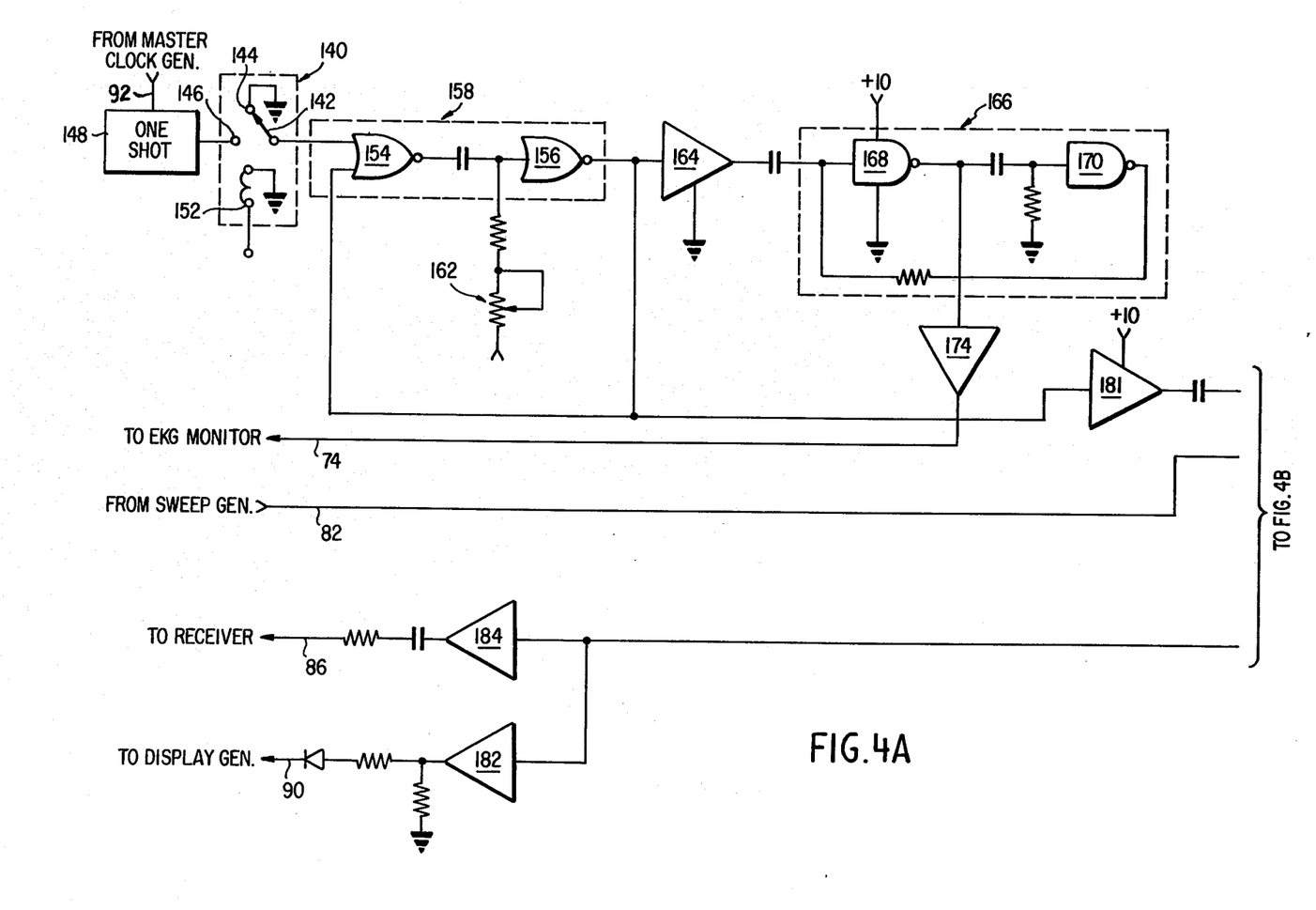
FIGS. 4A and 4B together are a schematic diagram of the EKG logic circuit used in the system illustrated in FIG. 2.
Figure 4B:
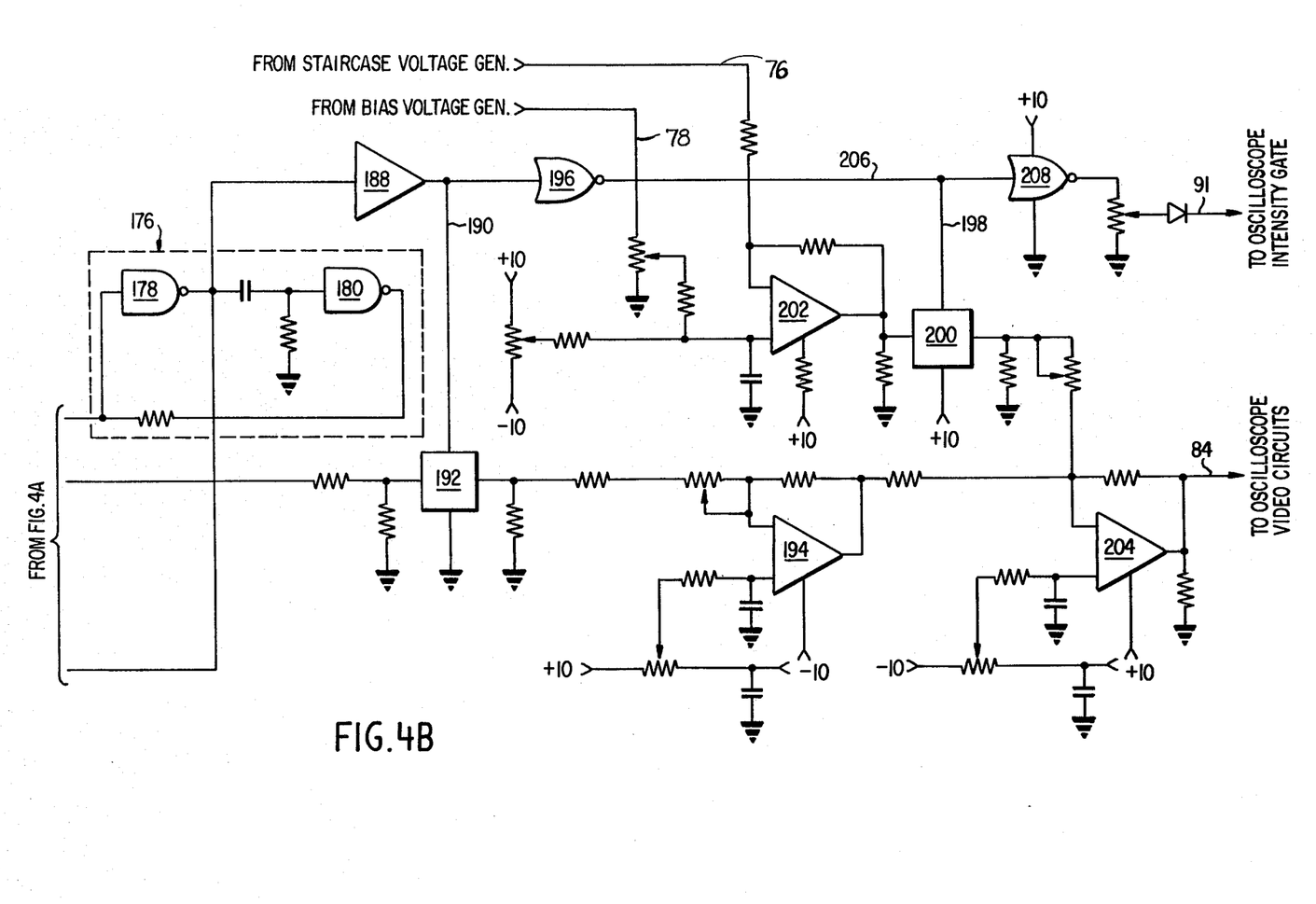

Attention is now directed to FIGS. 4a and 4b wherein the details of the EKG logic circuit are illustrated. It is noted that the waveforms controlled by this circuit are illustrated in FIGS. 5 and 6. The purpose of the EKG logic circuit 64 is to allow the cross sectional image of the heart and EKG waveforms to presented together in real time. In this regard it is noted that one frame of the cross-sectional image of the heart produced by the C-scan ultrasonoscope is generated in 48 milliseconds while a complete EKG waveform requires at least one full second, and possibly several seconds to develop fully. Thus a problem exists in presenting both images together in real time on a single cathode ray tube display.

Referring again to FIG. 4, an EKG activating switch 140 is shown for energizing the EKG logic circuit. The EKG activating switch 140 may also be equipped with the other contacts required to switch in the entire EKG display circuitry of the invention, that is to switch an ultrasonoscope between conventional C-scan display only and C-scan display combined with the EKG trace. When the switch 140 is in the position shown, the switch armature 142 is connected with terminal 144 which is grounded, thereby disabling the EKG logic circuit. When the armature 142 is moved into contact with terminal 146, the armature is coupled to a one shot multivibrator 148 which is in turn coupled to the master clock generator 16 over a line 92. Activation of the EKG switch also activates a relay 152 which applies power to the EKG logic circuitry 64, the EKG monitor circuit 62 and also provides the means of switching these circuits into the ultrasonoscope system.

Figure 5A:
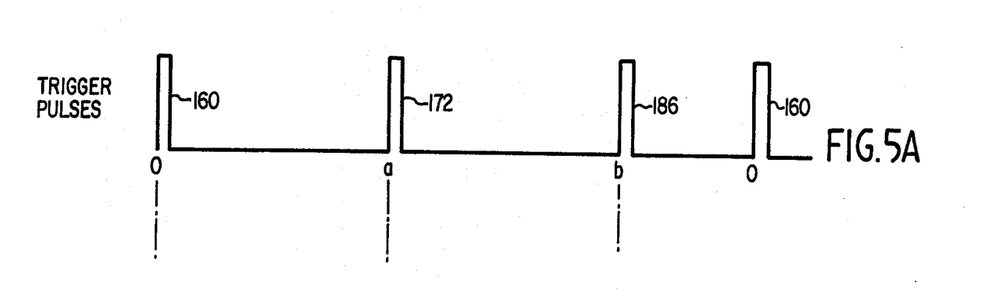
FIG. 5A is a timing diagram illustrating triggering pulses.
Figure 6A:
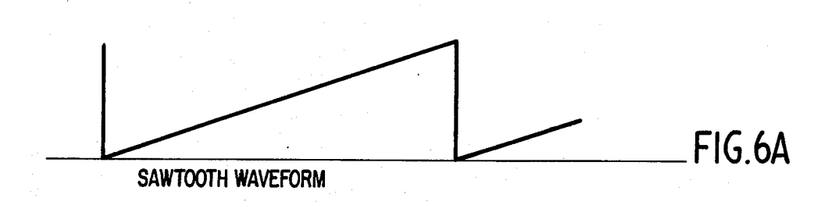
FIG. 6A is a diagram of a sawtooth waveform.
Figure 6B:
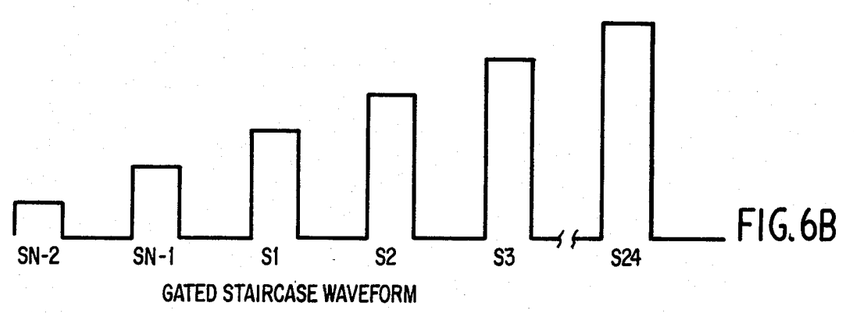
FIG. 6B is a diagram of a gated staircase waveform.
Figure 6C:
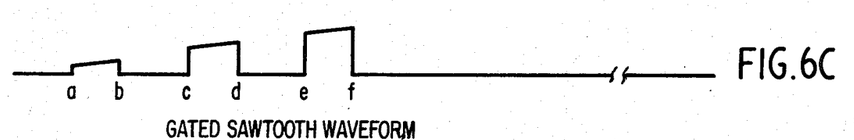
FIG. 6C is an illustration of a gated sawtooth waveform.

The switch armature 142 is coupled to one input of a NAND gate 154 which is capacitively coupled to a second NAND gate 156, the two NAND gates being connected together so as to form a one shot pulse generator 158 creating a pulse having a width equal to one-half the time between the zero clock pulses 160 shown in FIG. 5A. The one shot pulse generator 158 includes biasing and delay control circuitry 162.

The output of the pulse generator 158 is passed through a buffer amplifier 164 and is capacitively coupled to a narrow one shot pulse generator 166 formed of interconnected NAND gates 168 and 170. The narrow pulse generator 166 produces a pulse 172 delayed by an interval a relative to the zero pulse 160, as shown in FIG. 5A. This pulse is fed through a buffer amplifier 174 to line 74 which applies to it the EKG monitor circuit for triggering that circuit.

Figure 5B:
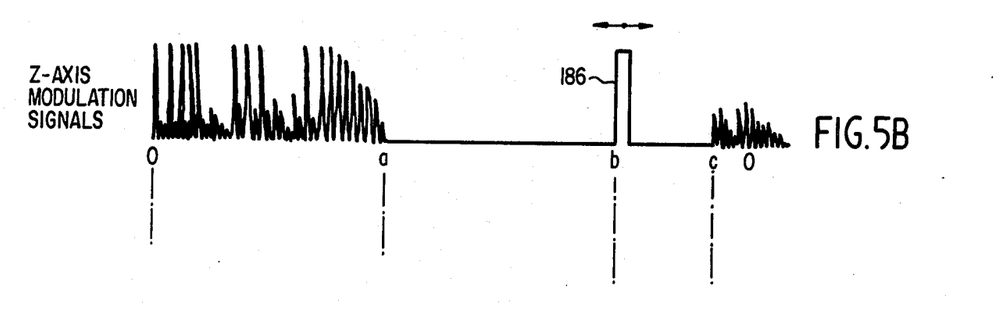
FIG. 5B is a graphical display of modulation and blanking in accordance with the EKG display of the present invention.
Figure 5C:
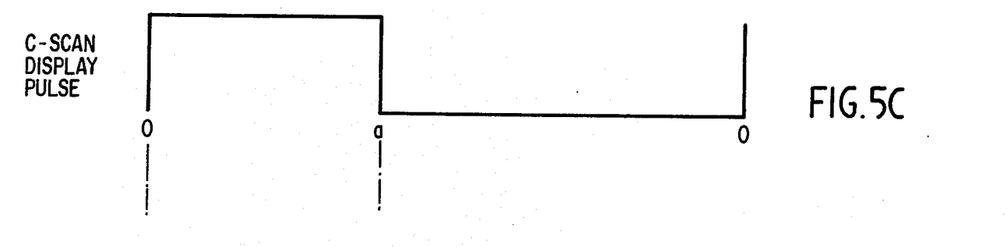
FIG. 5C is a timing diagram illustrating a C-scan display pulse.

It is noted that the display duration of the CRT tube 44 is normally controlled by the display generator 88 shown in FIG. 2. The normal display generator pulse is illustrated in FIG. 5C as extending over the time interval from zero to a. This display pulse establishes the duration of the region 10 display on the CRT, and has a duration less than half the period of the master clock generator 16 as represented by the 0 to 0 interval in FIGS. 5A–5B. With the EKG circuitry activated, a second display pulse, shown in FIG. 5D as extending over the time interval a–c is provided by a one shot pulse generator 176 formed of interconnected NAND gates 178 and 180. The pulse generator 176 receives its triggering input from pulse generator 158 through a buffer amplifier 181, and is connected in parallel with pulse generator 166. The display pulse illustrated in FIG. 5C serves to start the region 10 display at the left edge of the CRT before the next pulse from master clock generator 16. The second display pulse is coupled through buffer amplifier 182 to line 90 which applies it to the display generator 88. The same pulse is also applied through a parallel buffer amplifier 184 to line 86 through which it is applied to the receiver 36 for momentarily turning off the gain to eliminate noise modulation from the Z-axis input of the CRT as shown in FIG. 5B. This enables the position-modulated EKG pulse 186 to be displayed during a noise-free interval. The same pulse is similarly applied through a third parallel buffer amplifier 188 and a line 190 to an analog gate 192 for opening the gate.

The analog gate 192 receives a sawtooth or ramp input, as shown in FIG. 6A over line 82 from sweep generator 80. A portion of this waveform is passed through the analog gate 192 by the gating voltage and applied to a summing amplifier 194 to produce an output waveform which is shown in FIG. 6C.

Figure 5D:
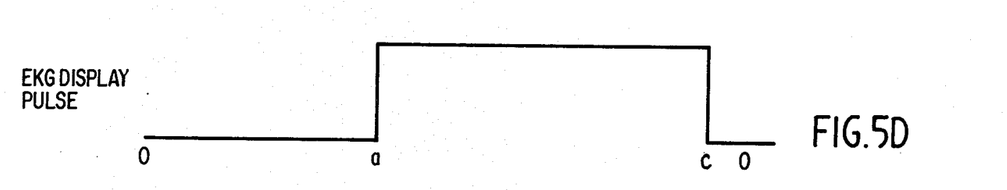
FIG. 5D is a timing diagram illustrating an EKG display pulse.

The EKG display pulse of FIG. 5D is simultaneously applied through a buffer amplifier 196 and a line 198 to a second analog gate 200 for the purpose of closing this gate. The analog input of the gate 200 is the voltage from staircase generator 46 and the voltage from the bias generator 48 which are added together in a summing amplifier 202. This combined voltage is the raster staircase voltage. The EKG display pulse disables the analog gate 200, shutting off the staircase voltage and resulting in a waveform as shown in FIG. 6B.

The output of the analog gate 200 is summed with the output of analog gate 192 and amplifier 194 by a third summing amplifier 204, and the summed output is applied via line 84 to the oscilloscope video circuits 40. This voltage generates on the screen of the CRT 44 a 24 line raster for forming the C-scan image and a trace sweeping slowly from bottom to top of the CRT for displaying the EKG waveform.

To control the intensity of the sweeping trace, the EKG display pulse of FIG. 5D is passed through buffer amplifier 196 over a line 206 to an additional buffer amplifier 208, and is then applied via line 91 to the intensity gate 138.

The previously mentioned EKG trigger pulse 172 of FIG. 5A is passed through buffer amplifier 174, as previously mentioned, and supplied to the EKG monitor circuit 62 which translates the EKG signal from a horizontal display to a vertical display triggered and synchronized by the pulse 172. The translated EKG signal is the previously mentioned pulse 186 occurring at the time interval b, as shown in FIGS. 5A and 5B. This pulse moves horizontally with the EKG voltage waveform which is coupled to the intensity gate 138 of the oscilloscope 142. The result is a spot moving vertically and modulated to the left and right by the incoming EKG information. The vertical EKG motion is generated by the gated sawtooth waveform illustrated in FIG. 6C. Accordingly, a real time display of both heart and EKG waveforms is possible by use of the apparatus of the present invention.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An improved biomedical diagnostic instrument including an ultrasonoscope system for simultaneously displaying a cross-sectional image of an internal organ and an EKG waveform on a single cathode ray tube, comprising:

a plurality of ultrasonic transducer means arranged in a row and adapted to be positioned on a patient's body for transmitting ultrasonic impulses into and receiving reflected ultrasonic impulses from said internal organ, control means coupled to said transducer means for sequentially energizing said transducer means, receiver means coupled to said transducer means for receiving said reflected ultrasonic impulses, cathode ray tube display means coupled to said receiver means for displaying said cross-sectional image of said internal organ, EKG monitor circuit means including electrodes adapted to be coupled to said patient for monitoring biological electrical signals thereof, EKG logic circuit means coupled to said EKG monitor circuit means, to said receiver means and to said cathode ray tube display means for enabling simultaneous real-time display of both said cross-sectional image of said internal organ and said EKG waveform on said cathode ray tube, said EKG logic circuit means including first, second and third interconnected one-shot pulse generators for producing pulses of predetermined duration, and first and second analog gating means for respectively gating first and second analog signals therethrough, said third one-shot pulse generator being coupled to said first and second analog gating means for controlling the passage of said analog signals, said second and third one-shot pulse generators being connected in parallel to the output of said first one-shot pulse generator for triggering by said first one-shot pulse generator, said cathode ray tube means including a sweep generator and a staircase voltage generator, said first analog gating means being coupled to said sweep generator for gating the output thereof, said second analog gating means being coupled to said staircase voltage generator for gating the output thereof, and summing amplifier means coupled to said first and second analog gating means for summing the gated outputs thereof.

2. An improved biomedical diagnostic instrument for the real time, synchronized, simultaneous display of a cross-sectional image of an internal organ and an EKG waveform on a cathode ray tube, comprising:

a plurality of ultrasonic transducer elements arranged in a row and adapted to be positioned on a patient's body for transmitting ultrasonic impulses into and receiving echo signals from said internal organ;

means for sequentially energizing said transducer elements and transmitting ultrasonic impulses to said organ;

a single-gun cathode ray tube display means coupled to said transducer elements for displaying a cross-sectional image of said internal organ in a C-scan mode;

an EKG monitor circuit means for deriving an EKG signal from said patient and converting said signal to a train of coded pulses;

a logic circuit means coupled to said EKG monitor circuit means and said display means for enabling the simultaneous real time display of said cross-sectional image and said EKG waveform on said display means, the frame period of said EKG waveform being much longer than the frame period of said cross-sectional image whereby said EKG waveform and said cross-sectional image are in synchronization, that is, a viewer can discern what motion is taking place in the cross-sectional image for any particular point on the EKG waveform;

said logic circuit means including means for producing a vertical sweep voltage for said display means having a gated staircase waveform interleaved with a gated sawtooth waveform whereby the raster that forms the cross-sectional image moves vertically as a function of said gated staircase waveform and the raster that forms the EKG waveform moves vertically as a function of said sawtooth waveform.

3. An improved biomedical diagnostic instrument for the real time, synchronized, simultaneous display of a cross-sectional image of an internal organ and an EKG waveform on a cathode ray tube, comprising:

a plurality of ultrasonic transducer elements arranged in a row and adapted to be positioned on a patient's body for transmitting ultrasonic impulses into and receiving echo signals from said internal organ;

means for sequentially energizing said transducer elements and transmitting ultrasonic impulses to said organ;

a single-gun cathode ray tube display means coupled to said transducer elements for displaying a cross-sectional image of said internal organ in a C-scan mode;

an EKG monitor circuit means for deriving an EKG signal from said patient and converting said signal to a train of coded pulses;

a logic circuit means coupled to said EKG monitor circuit means and said display means for enabling the simultaneous real time display of said cross-sectional image and said EKG waveform on said display means, the frame period of said EKG waveform being much longer than the frame period of said cross-sectional image whereby said EKG waveform and said cross-sectional image are in synchronization, that is, a viewer can discern what motion is taking place in the cross-sectional image for any particular point on the EKG waveform;

said logic circuit means including first and second analog gates, means for alternately generating first and second analog gate control signals, means for coupling said first and second analog gate control signals to said first and second analog gates, respectively, and a summing amplifier;

said cathode ray tube display means including a sawtooth voltage generator and a staircase voltage generator;

said first analog gate being coupled to said sawtooth voltage generator for gating the output thereof in accordance with said second analog gate control signal whereby a gated staircase waveform is produced; and said gated sawtooth waveform and said gated staircase waveform being summed by said summing amplifier and the vertical sweep of the raster of the cathode ray tube display means being a function of the output of said summing amplifier.

4. An improved biomedical diagnostic instrument for the real time simultaneous display of a cross-sectional image of an internal organ in C mode and an EKG waveform on a cathode ray tube, comprising:

a plurality of ultrasonic transducer elements arranged in a row and adapted to be positioned on a patient's body for transmitting ultrasonic impulses into and receiving echo signals from said internal organ;

means for sequentially energizing said transducer elements and transmitting ultrasonic impulses to said organ;

an EKG circuit means including body electrodes, an amplifier and two pulse generators deriving an EKG signal from said patient and converting said signal to a train of coded pulses;

a single-gun cathode ray tube;

means coupled to said cathode ray tube for generating a horizontal sweep voltage;

means for producing a CRT vertical sweep voltage having a gated staircase waveform interleaved with a gated sawtooth waveform, said sweep voltage means comprising means for repetitively generating a staircase voltage, means for repetitively generating a sawtooth voltage, and a logic circuit, said logic circuit alternately gating said staircase voltage and said sawtooth voltage and mixing said two gated voltages;

means for coupling said vertical sweep voltage means to said cathode ray tube;

means for coupling said received echo signals and said coded pulses to said cathode ray tube, the raster of said cathode ray tube being intensity modulated by said echo signals and said coded pulses whereby said cathode ray tube simultaneously displays said cross-sectional image and said EKG waveform.

5. An instrument as in claim 4 wherein said sawtooth voltage has a period much longer than the period of said staircase voltage to enable a cathode ray tube viewer to visually synchronize said EKG waveform with said cross-sectional image.

6. An instrument as set forth in claim 5 wherein the sawtooth voltage period is at least one second and 20 times as great as the staircase voltage period.

7. An instrument as recited in claim 4 wherein means is included for controlling the width of said coded pulses, and said pulse width controls the width of the EKG waveform raster.

* * * * *